US008652452B2

(12) United States Patent
Delort et al.

(10) Patent No.: US 8,652,452 B2

(45) Date of Patent: Feb. 18, 2014

(54) 2,4-DISUBSTITUTED PYRIDINES AS PERFUMING INGREDIENTS

(75) Inventors: Estelle Delort, Geneva (CH); Kirk F. Eidman, Newtown, PA (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/635,183

(22) PCT Filed: Mar. 10, 2011

(86) PCT No.: PCT/IB2011/050996

§ 371 (c)(1), (2), (4) Date: Sep. 14, 2012

(87) PCT Pub. No.: WO2011/121469

PCT Pub. Date: Oct. 6, 2011

(65) Prior Publication Data

US 2013/0004447 A1 Jan. 3, 2013

Related U.S. Application Data

(60) Provisional application No. 61/318,523, filed on Mar. 29, 2010.

(30) Foreign Application Priority Data

Apr. 7, 2010 (EP) .................................... 10159260

(51) Int. Cl.

| | |
|---|---|
| ***A61K 8/00*** | (2006.01) |
| ***A61K 8/18*** | (2006.01) |
| ***A61Q 15/00*** | (2006.01) |
| ***A61K 8/02*** | (2006.01) |
| ***A01N 25/34*** | (2006.01) |

(52) U.S. Cl.
USPC .............................. 424/65; 424/401; 424/402

(58) Field of Classification Search
USPC ............................................................ 424/65
See application file for complete search history.

(56) References Cited

U.S. PATENT DOCUMENTS

| | | | | |
|---|---|---|---|---|
| 4,113,645 A * | 9/1978 | DeSimone | ............... | 252/186.44 |
| 5,214,027 A | 5/1993 | Ishihara et al. | ................. | 512/10 |
| 6,426,112 B1 * | 7/2002 | Boatright | ...................... | 426/634 |
| 2010/0130624 A1 | 5/2010 | Oertling | ........................ | 514/788 |
| 2011/0020518 A1 | 1/2011 | Delort et al. | .................. | 426/537 |

FOREIGN PATENT DOCUMENTS

| | | | |
|---|---|---|---|
| EP | 2 100 589 A1 | | 9/2009 |
| WO | WO 2009/122318 A1 | | 10/2009 |
| WO | WO 2009122318 A1 | * | 10/2009 |

OTHER PUBLICATIONS

Zhou et al. (Analysis of Volatile Compounds and Their Contribution to Flavor in Cereals, Oct. 1999, Journal of Agricultural and Food Chemistry, vol. 47, pp. 3941-3953).*

Pyrazine Specialties, (Jan. 2008, pp. 1-78).*

International Search Report and Written Opinion, application No. PCT/IB2011/050996, mailed May 23, 2011.

Fife et al., "Regioselective Cyanation of Pyridine 1-Oxides with Trimethylsilanecarbonitrile: A Modified Reissert-Henze Reaction," J. Org. Chem., 48:1375-1377 (1983).

Fontana et al., "Homolytic Alkylation of Heteroaromatic Bases: The Problem of Monoalkylation," Tetrahedron, 46(7):2525-2538 (1990).

Huang-Minion, "A Simple Modification of the Wolff-Kishner Reduction," J. Am. Chem. Soc., 68(12):2487-2488 (1946).

Ishihara et al., "New Pyridine Derivatives and Basic Components in Spearmint Oil (*Mentha* gentilis f. cardiac) and Peppermint Oil (*Mentha piperita*)," J. Agric. Food Chem., 40:1647-1655 (1992).

Kaiser, "New Natural Products of Structural and Olfactory Interest Identified in Fig Leaf Absolute (*Ficus carica* L.)", Progress in Essential Oil Research, Walter de Gruyter & Co., Berlin, pp. 227-239 (1986).

Nikishin et al., "Solvent-free alkylation of N-heteroaromatic compounds by RCOOH-Pb$(OAc)_4$ system," Russian Chemical Bulletin, International Edition, 54(4):997-1002 (Apr. 2005).

Shuman et al., "An Improved Synthesis of Homoproline and Derivatives," J. Org. Chem., 55:738-741 (1990).

Teague et al., "Some Pyridylhydantoins," J. Am. Chem. Soc., 75(14):3429-3430 (1953).

* cited by examiner

*Primary Examiner* — Brian-Yong Kwon
*Assistant Examiner* — Mark V Stevens
(74) *Attorney, Agent, or Firm* — Winston & Strawn LLP

(57) ABSTRACT

The present invention relates to the field of perfumery. More particularly, it concerns the use as perfuming ingredients of a 2,4-dialkyl-pyridine of formula (I):

(I)

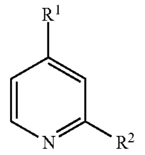

in the form of any one of its stereoisomers or a mixture thereof, wherein $R^1$ represents a $C_{1-3}$ alkyl group; $R^2$ represents a $C_{4-9}$ linear alkyl group; and the compound has between 10 and 15 carbon atoms. These compounds are useful for imparting odors of the green and/or pyrazine type. The present invention concerns the use of such compounds in the perfumery industry as well as the compositions or articles containing them.

9 Claims, No Drawings

2,4-DISUBSTITUTED PYRIDINES AS PERFUMING INGREDIENTS

This application is a 371 filing of International Patent Application PCT/IB2011/050996, filed Mar. 10, 2011, and claims the benefit of U.S. provisional application No. 61/318,523 filed on Mar. 29, 2010.

TECHNICAL FIELD

The present invention relates to the field of perfumery. More particularly, it concerns the use as perfuming ingredients of some 2,4-dialkyl-pyridines. The present invention concerns the use of said compounds in the perfumery industry as well as the compositions or articles containing said compounds.

PRIOR ART

Some pyridines are known as being potentially useful as perfuming ingredient, but only rare examples of 2,4-disubstituted pyridines have been reported.

In particular some 2,4-disubstituted pyridines are disclosed by Ishihare et al. (*J. Agric. Food Chem.,* 1992, 40, 1647) which are described as having an odor of the ozone (i.e. marine) or earthy type. Also, other 2,4-disubstituted pyridines are reported by Kaiser et al. (*Progress in Essential oil research,* 1986, 227) as having a tobacco like odor. All these prior art pyridines have substituents which are short chain or short branched groups in position 2 of the pyridinic ring, i.e. are compounds chemically different for the ones of the present invention.

In any case the odor properties of these prior art compounds are significantly different from the one of the present invention.

Another example of prior art pyridines are the 4-alkyl pyridines reported in EP 2100589 and having a marine odor. Alternatively it is also useful to mention 2-pentyl pyridine known for a use as flavor ingredient in meat applications and as having a vegetative, oily, mushrooms odor (Perfumery & Flavorist, 2006, 47). Once again the odor of the prior art compounds is quite different from the one of the present invention.

To the best of our knowledge, only few pyridines of the present invention have ever been reported in the prior art. In particular 4-methyl-2-pentyl-pyridine is mentioned in WO 09/122,318 as having a flavor of the fruity, woody type. 4-ethyl-2-butyl-pyridine is reported in *Tetrahedron,* 1990, 46, 2525 as chemical intermediate. 4-methyl-2-heptyl-pyridine is reported in *Russian chemical bulletin,* 2005, 54, 997 as chemical intermediate. However, these prior art documents do not report or suggest any olfactive properties of the compounds of formula (I), or any use of said compounds in the field of perfumery.

DESCRIPTION OF THE INVENTION

We have now surprisingly discovered that a compound of formula (I)

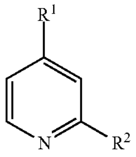

in the form of any one of its stereoisomers or a mixture thereof, and wherein $R^1$ represents a $C_{1-3}$ alkyl group;

$R^2$ represents a $C_{4-9}$ linear alkyl group; and said compound has between 10 and 15 carbon atoms;

can be used as perfuming ingredient, for instance to impart odor notes of the green and/or pyrazine type.

According to a particular embodiment of the invention, $R^1$ represents a $C_{1-3}$ linear alkyl group, or even a methyl or n-propyl group.

According to a particular embodiment of the invention, $R^2$ represents a $C_{5-8}$ linear alkyl group. $R^2$ may also represent a $C_5$, $C_6$ or $C_7$ linear alkyl group.

According to any one of the above embodiments of the invention, said compounds (I) have an odd number of carbon, e.g. $C_{11}$, $C_{13}$ or $C_{15}$ compounds.

As specific examples of the invention's compounds, one may cite, as non-limiting example, 4-methyl-2-pentyl-pyridine which possesses an odor having a green, green bean note, as well as a spicy-bell pepper, paprika note, and a green, pyrazinic bottom note. This compound is very interesting for its natural green, spicy-bell pepper character, which represents a novel aspect of green notes in general since it is sweeter, less aggressive and rooty than the known pyrazines or pyridines used in perfumery.

Moreover, 4-methyl-2-pentyl-pyridine can be used as substituent for natural extracts of bell pepper which are strongly irritant and forbidden in perfumery.

When the odor of 4-methyl-2-pentyl-pyridine is compared to the one of the known flavor ingredient 2-pentyl-pyridine, then the one of the present invention's compound distinguishes itself by lacking the acidic green notes, as well as the oily, solvent and mushroom notes so characteristic of 2-pentyl-pyridine. Moreover, 2-pentyl-pyridine odor does not possess at all a spicy olfactive character.

As other example, one may cite 4-n-propyl-2-pentyl-pyridine, which possesses an odor characterized by a very natural green, green peas note with a violet, powdery aspect.

As other specific, but non-limiting, examples of the invention's compounds, one may cite the following ones in Table 1:

TABLE 1

Invention's compounds and their odor properties

| Compound structure and name | Odor notes |
|---|---|
| 4-i-propyl-2-pentyl-pyridine | Green, pyrazine, fairly natural odor |
| 4-n-propyl-2-heptyl-pyridine | Green, pyrazine, bean odor |
| 4-n-propyl-2-butyl-pyridine | Green, pyrazine odor |
| 4-methyl-2-hexyl-pyridine | Green, pyrazine, bean odor |
| 4-ethyl-2-hexyl-pyridine | Green, bean, spicy-bell pepper, paprika note, pyrazine |
| 4-ethyl-2-pentyl-pyridine | Green, pyrazine odor |

According to a particular embodiment of the invention, the compounds of formula (I) are 4-methyl-2-pentyl-pyridine or 4-n-propyl-2-pentyl-pyridine or 4-ethyl-2-hexyl-pyridine.

When the odor of the invention's compounds is compared with that of the prior art compounds, mentioned above, then the invention's compounds distinguish themselves by clearly having a totally different odor, by lacking the marine or tobacco character of the prior art compounds, as well as by lacking the meaty and/or acidic of 2-pentyl pyridine.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and ii) a perfumery consumer base;

is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer bases can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 15% by weight, or even more, of the compounds of the invention based on the weight of the composition into which they are incorporated. Concentrations lower than these, such as in the order of 0.01% to 3% by weight, can be used when these compounds are incorporated into perfumed articles, percentage being relative to the weight of the article.

The invention's compounds can be prepared according to a method comprising a reaction between the 2-chloro or bromo-4-alkyl-pyridine and a Grignard reagent of the desired 2-alkyl chain, as described in the Examples herein below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) preparation of 4-methyl-2-pentyl-pyridine

A 50 ml reactor under argon was charged with 2-bromo-4-methylpyridine and THF. The reaction was cooled to −78° C. and the $Pd(dppf)_2Cl_2$ (dppf being 1,1'-di(diphenylphosphine)-ferrocene) catalyst was added, followed by 3.0 M pentyl magnesium bromide. The reaction was allowed to warm to 0° C. until the starting material was consumed. The reaction was quenched with 20 ml of saturated ammonium chloride solution and extracted with 20 ml of ethylacetate. The ethyl acetate layer was extracted with 20 ml of 1 M aqueous hydrochloric acid to extract the pyridine product from neutral organics. The aqueous acid layer was neutralized with 1 M NaOH and extracted with 20 ml of ethyl acetate. The ethyl acetate layer was washed with brine and dried on anhydrous sodium sulphate. The product phase was filtered and concentrated on the rotary evaporator to give 850 mg of product, a 44.9% yield.

$^1H$-NMR: 8.37 (d; 1H), 6.96 (s; 1H), 6.91 (d; 1H), 2.72 (dd; 2H), 2.30 (s; 3H), 1.72 (m; 2H), 1.34 (m; 4H), 0.89 (t; 3H)

$^{13}C$-NMR: 162.27; 148.91; 121.87; 38.28; 31.67; 29.67; 22.57; 20.98; 14.

b) preparation of 4-n-propyl-2-butyl-pyridine 4-n-propyl-pyridine was prepared by alkylation of 4-picoline with sodium amide suspended in liquid ammonia and ethyl iodide, as described in *Vogel's Textbook of Practical Organic Chemistry*, Fourth Edition, p 903. It was obtained in good yield (77%). 2-cyano-4-n-propyl-pyridine was obtained from 4-n-propyl-pyridine following the procedure described by Shuman et al. [*An Improved Synthesis of Homoproline and Derivatives* Robert T. Shuman, Paul L. Ornstein, Jonathan W. Paschal, and Paul D. Gesellchen, *J. Org. Chem.* 1990, 55, 738-741]. In a first step, 4-n-propyl-pyridine (1 eq.) was converted into 4-n-propyl-pyridine N-oxide in glacial acetic acid, 30% hydrogen peroxide (1 eq.). Then, 4-n-propyl-pyridine N-oxide was converted into 2-cyano-4-n-propyl-pyridine in good yield (72%) with a modification of the Reissert-Henze reaction, reported by Fife [Fife, W. K. *J. Org. Chem.* 1983, 48, 1375.] 1-(4-propylpyridine-2-yl)pentan-1-one was obtained by treating the pyridyl cyanide with a small excess of the corresponding butyl magnesium iodide, as described by Teague et al. [*Some Pyridylhydantoins* P. C. Teague; A. R. Ballentine, G. L. Rushton *J. Am. Chem. Soc* 1953, 75, 3429-3430]. The ketone was separated from the reaction mixtures by extraction with chloroform, and obtained in relatively good yield (60%). 4-n-propyl-2-butyl-pyridine was obtained in high yield (85%) by a modified Wolff-Kishner reduction, as described by Huang-Minlon [*A Simple Modification of the Wolff-Kishner Reduction*, Huang-Minlon *J. Am. Chem. Soc* 1946, 68, 2487-2488].

$^1H$-NMR: 8.39 (d, J=5.2 Hz, 1H); 6.95 (s, 1H); 6.90 (dd, J=5.2, 1.6 Hz, 1H); 2.75 (m, 2H), 2.54 (m, 2H) 1.76-1.59 (m, 4H); 1.39 (m, 2H), 0.97-0.91 (m, 6H).

$^{13}C$ NMR: 13.7 (q), 14.0 (q), 22.6 (t), 23.5 (t), 32.2 (t), 37.3 (t), 38.1 (t), 121.2 (d), 122.9 (d), 149.0 (d), 151.6 (s), 162.3 (s).

c) preparation of 4-n-propyl-2-pentyl-pyridine 4-n-propyl-2-pentyl-pyridine was obtained with similar yields and in an identical manner to 4-n-propyl-2-butyl-pyridine (see above) except that the intermediates 1-(4-propylpyridine-2-yl)hexan-1-one was obtained by treating the pyridyl cyanide with a small excess of pentyl magnesium iodide.

$^{1}H$-NMR: 8.39 (d, J=5.2 Hz, 1H); 6.95 (s, 1H); 6.90 (dd, J=5.2, 1.6 Hz, 1H); 2.74 (m, 2H), 2.54 (m, 2H) 1.72 (mc, 2H), 1.65 (m, 2H); 1.40-1.30 (m, 4H), 0.94 (t, J=7.3 Hz, 3H), 0.89 (m, 3H).

$^{13}C$ NMR: 13.7 (q), 14.0 (q), 22.6 (t), 23.5 (t), 29.7 (t), 31.7 (t), 37.3 (t), 38.4 (t), 121.2 (d), 122.9 (d), 149.0 (d), 151.7 (s), 162.3 (s).

d) preparation of 4-n-propyl-2-heptyl-pyridine 4-n-propyl-2-heptyl-pyridine was obtained with similar yields and in an identical manner to 4-n-propyl-2-butyl-pyridine except that the intermediates 1-(4-propylpyridine-2-yl) octan-1-one was obtained by treating the pyridyl cyanide with a small excess of heptyl magnesium iodide respectively.

$^{1}H$-NMR: 8.42 (d, J=5.2 Hz, 1H); 6.99 (s, 1H); 6.94 (dd, J=5.2, 1.6 Hz, 1H); 2.78 (mc, 2H), 2.58 (m, 2H) 1.75 (m, 2H), 1.69 (m, 2H); 1.44-1.36 (m, 8H), 0.98 (t, J=7.3 Hz, 3H), 0.91 (m, 3H).

$^{13}C$ NMR: 13.7 (q), 14.1 (q), 22.7 (t), 23.6 (t), 29.2 (t), 29.4 (t), 30.0 (t), 31.8 (t), 37.3 (t), 38.4 (t), 121.2 (d), 122.9 (d), 149.0 (d), 151.7 (s), 162.3 (s).

e) preparation of 4-1-propyl-2-pentyl-pyridine 4-1-propyl-2-pentyl-pyridine was prepared according to the procedure described in [*A convenient Synthesis of the Monoalkylpyridines; a New Prototropic Reaction of* 3-*Picoline* H. C. Brown, W. A. Murphey *J. Am. Chem. Soc.* 1951, 73, 3308-12.]

$^{1}H$-NMR: 8.40 (d, J=5.2 Hz, 1H); 6.98 (s, 1H); 6.95 (dd, J=5.2, 1.6 Hz, 1H); 2.85 (m, 1H), 2.75 (m, 2H), 1.73 (m, 2H) 1.39-1.32 (m, 4H); 1.25 (d, J=6.9, 6H), 0.90 (m, 3H).

$^{13}C$ NMR: 14.0 (q), 22.6 (t), 23.2 (q), 29.7 (t), 31.7 (t), 33.6 (d), 38.5 (t), 119.2 (d), 120.9 (d), 149.1 (d), 157.8 (s), 162.5 (s).

f) 4-methyl-2-hexyl-pyridine

This compound was obtained using the same experimental procedure as per 4-methyl-2-pentyl-pyridine (see above), using hexyl magnesium bromide instead of pentyl magnesium bromide. The product was obtained with similar yield and purified in the same way.

$^{1}H$-NMR: 8.3 (d), 6.95 (s), 6.9 (d), 2.7 (t), 2.3 (s), 1.7 (q), 1.3 (m), 0.8 (m)

$^{13}C$ NMR: 162.31, 148.95, 147.14, 123.51, 121.86, 38.36, 31.74, 29.95, 29.15, 22.59, 20.97, 14.08 g) 4-ethyl-2-hexyl-pyridine

This compound was obtained using the same experimental procedure as per 4-methyl-2-pentyl-pyridine (see above), using hexyl magnesium bromide instead of pentyl magnesium bromide and 2-chloro-4-ethyl pyridine instead of 2-bromo-4-methylpyridine. The product was obtained with similar yield and purified in the same way.

$^{1}H$-NMR: 8.4 (d), 6.96 (s), 6.93 (d), 2.7 (t), 2.6 (q), 1.7 (m), 1.3 (m), 1.2 (t), 0.89 (t)

$^{13}C$ NMR: 162.40, 153.14, 149.06, 122.25, 120.59, 38.44, 31.74, 29.98, 29.17, 28.20, 22.59, 14.40, 14.08 h) 4-ethyl-2-pentyl-pyridine

This compound was obtained using the same experimental procedure as per 4-methyl-2-pentyl-pyridine (see above), using 2-chloro-4-ethyl pyridine instead of 2-bromo-4-methyl pyridine. The product was obtained with similar yield and purified in the same way.

$^{1}H$-NMR: 8.4 (d), 6.96 (s), 6.93 (d), 2.7 (t), 2.6 (q), 1.7 (m), 1.3 (m), 1.2 (t), 0.9 (t)

$^{13}C$ NMR: 162.40, 153.14, 149.06, 122.25, 120.59, 38.41, 31.71, 29.71, 28.20, 22.57, 14.40, 14.04

Example 2

Preparation of a Perfuming Composition

A perfuming composition, of the fig type, was prepared by admixing the following ingredients:

| Ingredient | Parts by weight |
|---|---|
| Cis-3-hexenol acetate | 20 |
| Benzyl benzoate | 890 |
| 10%* Cis-3-hexenol butyrate | 60 |
| Caryophyllene | 600 |
| Gamma decalactone | 40 |
| Gamma octalactone | 100 |
| Cis-3-hexenol | 30 |
| 1%* Sulfox | 80 |
| | 1820 |

*in dipropyleneglycol 1) methyl cis-dihydrojasmonate; origin: Firmenich SA, Geneva, Switzerland The addition of 180 parts by weight of 10%* 4-methyl-2-pentyl-pyridine to the above-described composition imparted to the latter a unique green, fig tree leaves aspect as well as a spicy, bell pepper connotation.

The addition of the same amount of 2-pentyl pyridine provided a very acidic green note with totally unacceptable mushroom, meaty notes.

Example 3

Preparation of a Perfuming Composition

A perfuming composition, of the citrus-herbaceous-woody type, was prepared by admixing the following ingredients:

| Ingredient | Parts by weight |
|---|---|
| Linalyl acetate | 30 |
| Vetyveryl acetate | 55 |
| Ethyl acetoacetate | 35 |
| Ambrettolide ® 1) | 90 |
| Ethylene brassylate 2) | 900 |
| Bergamote essential oil | 400 |
| 10%* Camphor | 30 |
| Cashmeran ® 3) | 25 |
| Cassis Base 4) | 45 |

-continued

| Ingredient | Parts by weight |
|---|---|
| 1%* Maltol | 50 |
| Dimethyl Benzyl Carbinyl Butyrate | 10 |
| 10%* Damascenone | 40 |
| Ethyl amyl ketone | 5 |
| 10%* Eucalyptus essential oil | 30 |
| Geraniol | 70 |
| Heliopropanal [5)] | 60 |
| Hydroxycitronellal | 30 |
| Iso E Super ® [6)] | 900 |
| Jasmal ® [7)] | 45 |
| Linalool | 65 |
| 10%* Oak moss essential oil | 50 |
| Hedione ® [8)] | 870 |
| Gamma octalactone | 10 |
| Phenethylol | 45 |
| Cis-3-hexenol | 10 |
| | 3900 |

*in dipropyleneglycol

[1)] 16-hexadecanolide; origin: Firmenich SA, Geneva, Switzerland

[2)] 1,4-dioxa-5,17-cycloheptadecanedione

[3)] 1,2,3,5,6,7-hexahydro-1,1,2,3,3-pentamethyl-4-indenone; origin: International Flavors & Fragrances, USA

[4)] Compounded specialty base; origin: Firmenich SA, Geneva, Switzerland

[5)] 3-(1,3-benzodioxol-5-yl)-2-methylpropanal; origin: Firmenich SA, Geneva, Switzerland

[6)] 1-(octahydro-2,3,8,8-tetramethyl-2-naphtalenyl)-1-ethanone; origin: International Flavors & Fragrances, USA

[7)] Mixture of 1,3-nonanediyl diacetate and tetrahydro-3-pentyl-4(2h)-pyranyl acetate; origin: International Flavors & Fragrances, USA

[8)] Methyl dihydrojasmonate; origin: Firmenich SA, Geneva, Switzerland

The addition of 100 parts by weight of 10%* 4-methyl-2-pentyl-pyridine to the above-described composition imparted to the latter very nice green connotation having a spicy-bell pepper aspect exalting the herbaceous note of the original composition, reinforcing thus the masculine character of the perfume.

The addition of the same amount of 2-pentyl pyridine imparted an acidic green note with totally unacceptable mushroom, meaty notes.

What is claimed is:

1. A method to confer, enhance, improve or modify the odor properties of a perfuming composition or of a perfumed article, which method comprises adding to said composition or article an effective amount of at least a compound of formula (I):

(I)

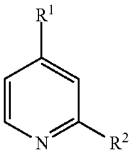

in the form of any one of its stereoisomers or a mixture thereof, and wherein $R^1$ represents a $C_{1-3}$ alkyl group; and $R^2$ represents a $C_{4-9}$ linear alkyl group;

wherein said compound has between 10 and 15 carbon atoms, and imparts odor notes of the green and pyrazine type without imparting the meaty or acidic notes of 2-pentyl pyridine, and wherein said composition or article includes a perfuming carrier or perfumery base, and said composition or article is a perfume, a fabric care product, a body-care product, an air care product or a home care product.

2. The method according to claim 1, wherein $R^1$ represents a $C_{1-3}$ linear alkyl group.

3. The method according to claim 1, wherein $R^2$ represents a $C_{5-8}$ linear alkyl group.

4. The method according to claim 1, wherein said compound (I) is a $C_{11}$, $C_{13}$ or $C_{15}$ compound.

5. The method according to claim 1, wherein said compound (I) is 4-methyl-2-pentyl-pyridine or 4-n-propyl-2-pentyl-pyridine or 4-ethyl-2-hexyl-pyridine.

6. A perfuming consumer product comprising a perfuming composition incorporated in a perfume, a fabric care product, a body-care product, an air care product or a home care product, the composition comprising:

i) at least one compound of formula (I):

(I)

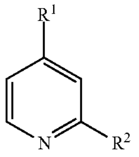

in the form of any one of its stereoisomers or a mixture thereof, and wherein $R^1$ represents a $C_{1-3}$ alkyl group; and $R^2$ represents a $C_{4-9}$ linear alkyl group;

wherein said compound has between 10 and 15 carbon atoms, and the at least one compound is present in an effective amount to impart odor notes of the green and pyrazine type without imparting the meaty or acidic notes of 2-pentyl pyridine;

ii) at least perfumery carrier; and iii) optionally at least one perfumery adjuvant.

7. A perfuming consumer product comprising:

i) at least one compound of formula (I):

(I)

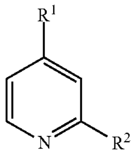

in the form of any one of its stereoisomers or a mixture thereof, and wherein $R^1$ represents a $C_{1-3}$ alkyl group; and $R^2$ represents a $C_{4-9}$ linear alkyl group;

wherein said compound has between 10 and 15 carbon atoms, and the at least one compound is present in an effective amount to impart odor notes of the green and pyrazine type without imparting the meaty or acidic notes of 2-pentyl pyridine; and ii) a perfumery consumer base that is a perfume, a fabric care product, a body-care product, an air care product or a home care product.

8. The perfuming consumer product according to claim 7, wherein the perfume, the fabric care product, the body-care product, the air care product or the home care product is one of a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

9. The perfuming consumer product according to claim 6, wherein the perfume, the fabric care product, the body-care product, the air care product or the home care product is one of a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

* * * * *